US010751359B2

(12) United States Patent
Kim et al.

(10) Patent No.: US 10,751,359 B2
(45) Date of Patent: Aug. 25, 2020

(54) NUCLEIC ACID APTAMER SPECIFICALLY BINDING TO AVIAN INFLUENZA VIRUS SUBTYPE H5 AND METHOD OF DETECTING AVIAN IFLUENZA VIRUS SUBTYPE H5 USING THE SAME

(71) Applicant: KOREA INSTITUTE OF SCIENCE AND TECHNOLOGY, Seoul (KR)

(72) Inventors: Byoung-Chan Kim, Seoul (KR); Sang-Kyung Kim, Seoul (KR); Seok Lee, Seoul (KR); Chang-Seon Song, Anyang-si (KR); Sang-Won Lee, Yongin-si (KR); Un-Jung Kim, Busan (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 371 days.

(21) Appl. No.: 15/679,610

(22) Filed: Aug. 17, 2017

(65) Prior Publication Data
US 2018/0050058 A1    Feb. 22, 2018

(30) Foreign Application Priority Data

Aug. 18, 2016 (KR) ........................ 10-2016-0104591

(51) Int. Cl.
*C12N 15/11* (2006.01)
*A61K 31/7088* (2006.01)
*C12N 15/115* (2010.01)
*C07K 14/005* (2006.01)

(52) U.S. Cl.
CPC ........ *A61K 31/7088* (2013.01); *C07K 14/005* (2013.01); *C12N 15/115* (2013.01); *C12N 2310/16* (2013.01); *C12N 2310/3517* (2013.01); *C12N 2760/10162* (2013.01); *C12N 2760/16163* (2013.01)

(58) Field of Classification Search
CPC .. C12N 15/111; C12N 15/115; C12N 2310/16
See application file for complete search history.

(56) References Cited

U.S. PATENT DOCUMENTS 9,683,030 B2    6/2017 Raguram et al.

FOREIGN PATENT DOCUMENTS

WO    2011/146825 A2    11/2011

OTHER PUBLICATIONS

Nguyen et al., Highly sensitive sandwich-type SPR based detection of whole H5Nx viruses using a pair of aptamers, Biosensors and Bioelectronics, vol. 86, pp. 293-300, available online on Jun. 21, 2016. (Year: 2016).*
H.G. Pereira et al.. New antigenic variants of avian influenza A viruses. Bull World Health Organ. 1966; 35(5): pp. 799-802.

* cited by examiner

*Primary Examiner* — Dana H Shin
(74) *Attorney, Agent, or Firm* — Goldilocks Zone IP Law

(57) ABSTRACT

This invention relates to a nucleic acid aptamer specifically binding to avian influenza virus subtype H5 and a method of detecting avian influenza virus subtype H5 using the same, and more particularly to a method of detecting avian influenza virus subtype H5, which is able to rapidly check the presence and concentration of avian influenza virus subtype H5 using a nucleic acid aptamer specifically binding to hemagglutinin, which is a surface protein of avian influenza virus subtype H5.

9 Claims, 6 Drawing Sheets
Specification includes a Sequence Listing.

A1(SEQ ID NO:1)

A2(SEQ ID NO:2)

A3(SEQ ID NO:3)

A4 (SEQ ID NO:4)

A5 (SEQ ID NO:5)

A6 (SEQ ID NO:6)

A7 (SEQ ID NO:7)

A8 (SEQ ID NO:8)

A9 (SEQ ID NO:9)

SEQUENCE LISTING

<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 1
agtgggttct tggtgcatcc caggagtacc                30

<210> SEQ ID NO 2
<211> LENGTH: 27
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 2
ggggtcaact tttcctttgt cggtttt                                    27

<210> SEQ ID NO 3
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 3
tggcagtggg ttgaggggaa gtcttattcg                                 30

<210> SEQ ID NO 4
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 4
tcacgctttt ggtgcatgca gagttttgtg                                 30

<210> SEQ ID NO 5
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 5
cttcttccac ccatgccggc tggagaatcc                                 30

<210> SEQ ID NO 6
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 6
tggattcacg cggtctccgc ccttgggtgg                                 30

<210> SEQ ID NO 7
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 7
tgggtttgga aattgggaca cagtggggcg                                 30

<210> SEQ ID NO 8
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

```
<400> SEQUENCE: 8
attgcaagga gaggctacgg ctatgacaga                                      30

<210> SEQ ID NO 9
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 9
tggattgcac gcaggggccg cttggctgtc                                      30

<210> SEQ ID NO 10
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 10
tgtcggggga acaatctgtg ttcgcttgtc                                      30

<210> SEQ ID NO 11
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 11
gcgaggttga gcgtgggcta cttggttcat                                      30

<210> SEQ ID NO 12
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 12
tgcacgcagg ggccgcttgg gtggagaggc                                      30

<210> SEQ ID NO 13
<211> LENGTH: 30
<212> TYPE: DNA
<213> ORGANISM: Artificial Sequence
<220> FEATURE:
<223> OTHER INFORMATION: AVIAN INFLUENZA VIRUS SUBTYPE H5 APTAMER

<400> SEQUENCE: 13
tacttatgtg ggccggtgcg tttgcatttt                                      30

<210> SEQ ID NO 14
<211> LENGTH: 19
<212> TYPE: DNA
<213> ORGANISM: Artificial Sequence
<220> FEATURE:
<223> OTHER INFORMATION: PRESERVED REGION OF ssDNA LIBRARY

<400> SEQUENCE: 14
gcaatggtac ggtacttcc                                                  19

<210> SEQ ID NO 15
```

```
<211> LENGTH: 24
<212> TYPE: DNA
<213> ORGANISM: Artificial Sequence
<220> FEATURE:
<223> OTHER INFORMATION: PRESERVED REGION OF ssDNA LIBRARY

<400> SEQUENCE: 15
caaaagtgca cgctactttg ctaa                                               24

<210> SEQ ID NO 16
<211> LENGTH: 19
<212> TYPE: DNA
<213> ORGANISM: Artificial Sequence
<220> FEATURE:
<223> OTHER INFORMATION: FORWARD PRIMER

<400> SEQUENCE: 16
gcaatggtac ggtacttcc                                                     19

<210> SEQ ID NO 17
<211> LENGTH: 24
<212> TYPE: DNA
<213> ORGANISM: Artificial Sequence
<220> FEATURE:
<223> OTHER INFORMATION: REVERSE PRIMER

<400> SEQUENCE: 17
ttagcaaagt agcgtgcact tttg                                               24
```

NUCLEIC ACID APTAMER SPECIFICALLY BINDING TO AVIAN INFLUENZA VIRUS SUBTYPE H5 AND METHOD OF DETECTING AVIAN IFLUENZA VIRUS SUBTYPE H5 USING THE SAME

CROSS REFERENCE TO RELATED APPLICATION

The present application claims the benefit of Korean Patent Application No. 10-2016-0104591 filed on Aug. 18, 2016.

BACKGROUND OF THE INVENTION

1. Field of the Invention

The present invention relates to a nucleic acid aptamer specifically binding to avian influenza virus subtype H5 and a method of detecting avian influenza virus subtype H5 using the same, and more particularly to a method of detecting avian influenza virus subtype H5, which is able to rapidly check the presence and concentration of avian influenza virus subtype H5 using a nucleic acid aptamer specifically binding to hemagglutinin, which is a surface protein of avian influenza virus subtype H5.

2. Description of the Related Art

Avian influenza is an acute epidemic disease caused by infection with avian influenza viruses, and avian influenza viruses may be classified into, depending on the type of pathogen, low pathogenic avian influenza viruses, which cause mild respiratory symptoms, have a death rate of 1 to 30% and lead to spawning degradation upon avian infections, and highly pathogenic avian influenza viruses, which show a high mortality rate of 95% or more. Based on the classification by the International Office of Epizootics, H5- and H7-subtype avian influenza viruses correspond to highly pathogenic avian influenza and are designated as major infectious disease sources due to their high risk. In particular, H5-subtype virus (e.g. H5N1 virus, etc.) is continuously reported to be associated with human infection, and influenza resulting from highly pathogenic avian influenza virus exhibits a high mortality rate of 60% or more upon human infection, unlike other influenza. Thus, early identification of the onset of avian influenza virus is regarded as very important in order to prevent avian influenza virus epidemics and resultant damage. Conventionally useful is an egg inoculation method in which a sample obtained from an avian is inoculated into the egg, incubated and then checked, as disclosed in the following Citation List.

CITATION LIST

Pereira H G, Lang G, Olesiuk O M, Snoeyenbos G H, Roberts D H, Easterday B C. New antigenic variants of avian influenza A viruses. Bull World Health Organ. 1966; 35(5):799~802.

In the detection method using an egg inoculation method, however, host cells have to be obtained, a processing time of 1 to 2 weeks or more is required due to cell culture, there is the likelihood of a virus propagating in the course of transporting a specimen to the laboratory from the location of an avian influenza outbreak, and culture testing has to be conducted in a special bio experimental facility (e.g. BSL3). Furthermore, detection requires a long period of time, and there are spatial limitations and the risk of secondary infection.

Hence, with the goal of effectively preventing avian influenza epidemics and the spread thereof, the need for a method of rapidly detecting avian influenza virus subtype H5 at an early stage is increasing.

SUMMARY OF THE INVENTION

Accordingly, the present invention has been made keeping in mind the above problems encountered in the related art, and the present invention is intended to provide a nucleic acid aptamer specifically binding to avian influenza virus subtype H5 and a method of detecting avian influenza virus subtype H5 using the same, wherein the presence and concentration of avian influenza virus subtype H5 may be rapidly detected using the nucleic acid aptamer specifically binding to hemagglutinin, which is a surface protein of avian influenza virus subtype H5.

Therefore, the present invention is realized by the following embodiments.

An embodiment of the present invention provides a nucleic acid aptamer specifically binding to hemagglutinin, which is a surface protein of avian influenza virus subtype H5, the nucleic acid aptamer having any one base sequence selected from among SEQ ID NOS: 1 to 13.

In the embodiment of the present invention, the nucleic acid aptamer may include a detectable label attached thereto.

In the embodiment of the present invention, the detectable label may be an optical label, an electrochemical label, a radioisotope or a combination thereof.

Another embodiment of the present invention provides a composition for detecting avian influenza virus subtype H5, comprising the aforementioned nucleic acid aptamer.

Still another embodiment of the present invention provides a sensor for detecting avian influenza virus subtype H5, comprising the aforementioned nucleic acid aptamer.

Yet another embodiment of the present invention provides a kit for detecting avian influenza virus subtype H5, comprising the aforementioned nucleic acid aptamer.

In the embodiment of the present invention, the kit may be provided in the form of a chip configured such that the nucleic acid aptamer is immobilized on the chip, or in the form of a microarray configured such that the nucleic acid aptamer is immobilized on a substrate.

A further embodiment of the present invention provides a method of detecting avian influenza virus subtype H5, comprising: bringing a sample into contact with the aforementioned nucleic acid aptamer, thus forming an avian influenza virus subtype H5-nucleic acid aptamer complex, measuring a signal from the avian influenza virus subtype H5-nucleic acid aptamer complex, analyzing the measured signal, thus detecting the presence or concentration of the avian influenza virus subtype H5 in the sample.

In the embodiment of the present invention, the method of detecting the avian influenza virus subtype H5 may further comprise separating the avian influenza virus subtype H5-nucleic acid aptamer complex from a reactant comprising the sample and the nucleic acid aptamer.

The present invention can exhibit the following effects.

According to the present invention, the presence and concentration of avian influenza virus subtype H5 can be rapidly detected using a nucleic acid aptamer specifically binding to hemagglutinin, which is a surface protein of avian influenza virus subtype H5.

BRIEF DESCRIPTION OF THE DRAWINGS

The above and other features and advantages of the present invention will be more clearly understood from the following detailed description taken in conjunction with the accompanying drawings, in which.

DESCRIPTION OF SPECIFIC EMBODIMENTS

Figure 1:
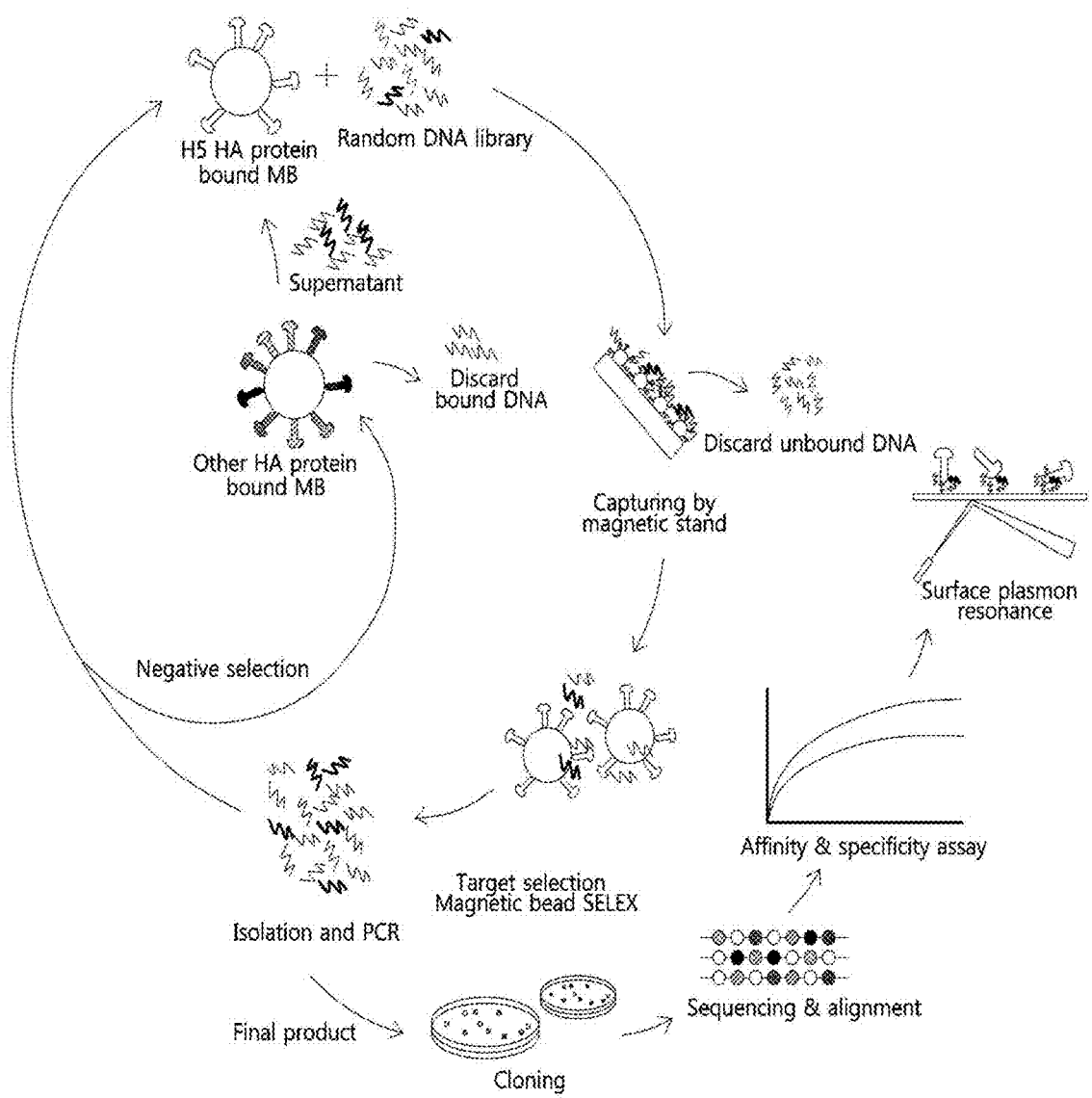
FIG. 1 is a reference view showing a Magnetic Cell-SELEX process for selecting a nucleic acid aptamer specifically binding to hemagglutinin, which is a surface protein of avian influenza virus subtype H5.

Hereinafter, a detailed description will be given of a nucleic acid aptamer specifically binding to avian influenza virus subtype H5 and a method of detecting avian influenza virus subtype H5 using the same according to the present invention, with reference to the appended drawings. Unless otherwise defined, all terms used herein have the same meaning as commonly understood by one of ordinary skill in the art to which the present invention belongs. If the meaning of the term used herein conflicts with the general meaning thereof, it accords to the definition used herein. In the following description of the present invention, detailed descriptions of known constructions and functions incorporated herein will be omitted when they may make the gist of the present invention unclear. As used herein, when any part "includes" any element, it means that other elements are not precluded but may be further included, unless otherwise mentioned.

An embodiment of the present invention addresses a single-stranded nucleic acid aptamer specifically binding to hemagglutinin (HA), which is a surface protein of avian influenza virus subtype H5. As used herein, the term "aptamer" refers to a nucleic acid molecule having a stable 3D structure and being able to bind to a target molecule at high affinity and specificity, and the term "specifically binding" means that the aptamer binds to any one kind of surface protein hemagglutinin of avian influenza virus subtype H5, and does not substantially bind to a non-target material including virus other than the avian influenza virus subtype H5 or shows a significant difference in affinity. The term "nucleic acid" refers to a nucleotide polymer, and may be used as the same meaning as oligonucleotide or polynucleotide. The nucleic acid includes deoxyribonucleotide (DNA), ribonucleotide (RNA) and/or peptide nucleic acid (PNA). The nucleotide is the basic constitutional unit of a nucleic acid molecule, includes DNA or RNA, and may include not only natural nucleotides but also analogues the sugar or base moiety of which is modified. Thus, the term "single-stranded nucleic acid" refers to nucleic acid in which the nucleotide polymer is present in the form of a single strand. The aptamer may specifically bind to the surface of avian influenza virus subtype H5 or to a portion of antigen protein. The term "surface of avian influenza virus subtype H5 or portion of antigen protein" may refer to all or part of the hemagglutinin protein that is present on the surface of avian influenza virus subtype H5.

The aptamer has any one base sequence selected from among SEQ ID NOS:1 to 13, and also may have a base sequence having sequence homology of 90% or more with any one base sequence selected from among SEQ ID NOS:1 to 13. Examples thereof may include base sequences of SEQ ID NOS:1 to 13, any base of which is subjected to substitution, insertion, deletion, addition or a combination thereof.

The aptamer may include a detectable label attached thereto. The detectable label may be a moiety that may be detected using any detection method known in the art. Examples of the detectable label may include an optical label, an electrochemical label, a radioisotope, and combinations thereof. The detectable label may be attached to a specific base or a specific structure of the aptamer, for example, a specific site of a hairpin-loop structure or a 3' or 5' terminus of an aptamer.

The optical label may be exemplified by a fluorescent material. For example, the fluorescent material may be selected from among fluorescein, 6-FAM, rhodamine, Texas Red, tetramethyl rhodamine, carboxyl rhodamine, carboxyl rhodamine 6G, carboxyl rhodol, carboxyl rhodamine 110, Cascade Blue, Cascade Yellow, coumarin, Cy2 (cyanine 2), Cy3, Cy3.5, Cy5, Cy5.5, Cy-chromium, phycoerythrin, PerCP (peridinin chlorophyll—a protein), PerCP-Cy5.5, JOE (6-carboxy-4',5'-dichloro-2',7'-dimethoxyfluorescin), NED, ROX (5-(and-6)-carboxy-X-rhodamine), HEX, Lucifer Yellow, Marina Blue, Oregon Green 488, Oregon Green 500, Oregon Green 514, Alexa Fluor, 7-amino-4-methylcoumarin-3-acetic acid, BODIPY FL, BODIPY FL-Br 2, BODIPY 530/550, conjugations thereof, and combinations thereof. Particularly useful as the fluorescent material is fluorescein, Cy3 or Cy5.

The optical label may be an enzyme, suitable for use in enzyme-linked immunosorbent assay (ELISA). The enzyme used for ELISA may include alkaline phosphatase, horseradish peroxidase, luciferase, or glucose oxidase. When the enzyme is used as the optical label, a chemiluminescent material may be employed in order to induce a chemiluminescent reaction, the chemiluminescent material being selected from among luminol, isoluminol, luciferin, lucigenin, 3-(2'-spiroadamantane)-4-methoxy-4-(3"-phosphoryloxy)phenyl-1,2-dioxetane (AMPPD), and disodium 3-(4-methoxyspiro {1,2-dioxetane-3,2'-(5'-chloro)tricyclo [3.3.1.13,7]decan}-4-yl)phenyl phosphate (CSPD). In addition thereto, any material appropriately selected by those skilled in the art is useful.

The optical label may be a fluorescence resonance energy transfer (FRET) pair, which includes a donor fluorophore and an acceptor fluorophore spaced apart from each other by an appropriate distance and in which the fluorescence emission of the donor is suppressed by the acceptor. The donor fluorophore may include FAM, TAMRA, VIC, JOE, Cy3, Cy5 and Texas Red. The acceptor fluorophore may be selected so as to overlap its excitation spectrum with the emission spectrum of the donor. The acceptor may be a non-fluorescence acceptor for quenching a wide range of donor.

The electrochemical label includes any electrochemical label known in the art, and may be exemplified by methylene blue. Another embodiment of the present invention addresses a composition for detecting avian influenza virus subtype H5, comprising a single-stranded nucleic acid aptamer specifically binding to hemagglutinin, which is a surface protein of avian influenza virus subtype H5. The composition includes at least one aptamer selected from the group consisting of an aptamer having a base sequence of SEQ ID NO:1 (hereinafter, referred to as "aptamer A1"), an aptamer having a base sequence of SEQ ID NO:2 (hereinafter, referred to as "aptamer A2"), an aptamer having a base sequence of SEQ ID NO:3 (hereinafter, referred to as "aptamer A3"), an aptamer having a base sequence of SEQ ID NO:4 (hereinafter, referred to as "aptamer A4"), an aptamer having a base sequence of SEQ ID NO:5 (hereinafter, referred to as "aptamer A5"), an aptamer having a base sequence of SEQ ID NO:6 (hereinafter, referred to as "aptamer A6"), an aptamer having a base sequence of SEQ ID NO:7 (hereinafter, referred to as "aptamer A7"), an aptamer having a base sequence of SEQ ID NO:8 (hereinafter, referred to as "aptamer A8"), an aptamer having a base sequence of SEQ ID NO:9 (hereinafter, referred to as "aptamer A9"), an aptamer having a base sequence of SEQ ID NO:10 (hereinafter, referred to as "aptamer A10"), an aptamer having a base sequence of SEQ ID NO:11 (hereinafter, referred to as "aptamer A11"), an aptamer having a base sequence of SEQ ID NO:12 (hereinafter, referred to as "aptamer A12"), and an aptamer having a base sequence of SEQ ID NO:13 (hereinafter, referred to as "aptamer A13"). The aptamer contained in the composition may have the aforementioned detectable label attached thereto.

The composition may further include an adjuvant that aids the formation of a complex in which the aptamer and hemagglutinin, which is a surface protein of avian influenza virus subtype H5, bind to each other, and examples thereof may include salmon sperm DNA, BSA, Tween-20, and/or PEG.

Still another embodiment of the present invention addresses a sensor for detecting avian influenza virus subtype H5, comprising a single-stranded nucleic acid aptamer specifically binding to hemagglutinin, which is a surface protein of avian influenza virus subtype H5. The sensor includes at least one aptamer selected from among aptamer A1 to aptamer A13, and the aptamer contained in the sensor may have the aforementioned detectable label attached thereto. For example, in the sensor including the aptamer containing the electrochemical label, due to structural changes in the aptamer bound to the target material, the label material becomes distant from or close to an electrode, or is separated from the aptamer, thus varying an electrochemical signal.

The sensor may be provided in the form of an array, including a substrate on which the aptamer is immobilized. The array is configured such that a plurality of specific molecules is immobilized at a predetermined portion on the substrate. The array may include a substrate and an immobilization region including the aptamer able to bind to avian influenza virus subtype H5 formed on the substrate. The aptamer may be covalently attached to the inside of the immobilization region. The aptamer may further include a plurality of compounds having functional groups that enable covalent bonding. As such, any functional group may be used so long as it enables the attachment of the aptamer. Examples of the functional group may include aldehyde, epoxy, carboxyl, and amine, and the compound may be siloxane having aldehyde, epoxy, carboxyl or amine at the end thereof. The substrate may be made of glass, silicon, polypropylene or polyethylene.

Yet another embodiment of the present invention addresses a kit for detecting avian influenza virus subtype H5, comprising a single-stranded nucleic acid aptamer specifically binding to hemagglutinin, which is a surface protein of avian influenza virus subtype H5. The kit may include at least one aptamer selected from among aptamer A1 to aptamer A13, and the aptamer contained in the kit may have the aforementioned detectable label attached thereto.

The kit may be provided in the form of a chip in which the aptamer is immobilized on a chip, or an array in which the aptamer is immobilized on a substrate. The immobilization of the nucleic acid aptamer on the chip or substrate may be performed using any process known in the art. For example, the chip or substrate is modified with streptavidin, the end of the aptamer is subjected to biotinylation, and immobilization may be conducted using the bonding of the biotin of the aptamer and the streptavidin of the support.

A further embodiment of the present invention addresses a method of detecting avian influenza virus subtype H5 using a nucleic acid aptamer specifically binding to hemagglutinin, which is a surface protein of avian influenza virus subtype H5. This detection method includes the steps of bringing a sample into contact with a single-stranded nucleic acid aptamer specifically binding to hemagglutinin, which is a surface protein of avian influenza virus subtype H5, thus forming an avian influenza virus subtype H5-aptamer complex, measuring a signal from the avian influenza virus subtype H5-aptamer complex, and analyzing the measured signal, thus detecting the presence or concentration of the avian influenza virus subtype H5 in the sample. In the method of the invention, at least one aptamer selected from among aptamer A1 to aptamer A13 may be used.

In the contact step, the sample is brought into contact with the single-stranded nucleic acid aptamer specifically binding to hemagglutinin, which is a surface protein of avian influenza virus subtype H5. The contact between the sample and the aptamer may be carried out in a reaction solution. For example, the contact may be carried out in a reaction solution including a salt in which the aptamer may efficiently bind to hemagglutinin of avian influenza virus subtype H5, an appropriate hydrogen ion concentration (pH) for maximizing reactivity, a solvent mixture to ensure homogeneity, and a factor for preventing non-specific binding. The solvent may include, for example, purified water, methanol, and acetonitrile. The factor for preventing non-specific binding may include, for example, salmon sperm DNA, BSA, Tween-20, and PEG. The appropriate pH may be, for example, 4 to 8, 5 to 7.5, or 6 to 7. The reaction temperature may be, for example, 15 to 50° C., 25 to 45° C., or 30 to 40° C. The reaction time may be, for example, 20 to 90 min, 30 to 80 min, or 50 to 70 min. The aptamer may be at least one selected from among aptamer A1 to aptamer A13, and the aptamer may have the aforementioned detectable label attached thereto.

In the signal measurement step, the signal is measured from the formed avian influenza virus subtype H5-aptamer complex, and the signal from the avian influenza virus subtype H5-aptamer complex may be generated by an optical label (e.g. a fluorescent material, an enzyme, etc.), an electrochemical label, or combinations thereof. The optical label (a fluorescent material) may be, for example, a donor-acceptor FRET pair. The optical label (an enzyme) may be horseradish peroxidase. The electrochemical label may be, for example, methylene blue.

In the detection step, the measured signal is analyzed to determine the presence or concentration of the avian influenza virus subtype H5 in the sample. The presence or concentration of the avian influenza virus subtype H5 in the sample may be determined in comparison with a control group. The control group may be an aptamer that does not bind to avian influenza virus subtype H5. For example, when the label attached to the aptamer is a donor-acceptor FRET pair, the control group may be an aptamer in which the fluorescence signal of the donor fluorophore is suppressed by the acceptor fluorophore. When the avian influenza virus subtype H5-aptamer complex is formed, the efficiency of FRET may decrease to thereby change the fluorescence signal. Based on changes in the signal, the presence or concentration of avian influenza virus subtype H5 may be checked. For example, when the label attached to the aptamer is an enzyme, the control group may be an enzyme attached to an aptamer that does not recognize the avian influenza virus subtype H5. When the avian influenza virus subtype H5-aptamer complex is formed, a color signal varies depending on changes in the enzyme substrate. On the other hand, when the avian influenza virus subtype H5-aptamer complex is not formed, the color signal does not vary, and thus, the presence or concentration of the avian influenza virus subtype H5 may be checked. For example, when the label attached to the aptamer is an electrochemical label, the control group may be an aptamer immobilized on an electrode. Due to changes in the structure of the aptamer bound to the avian influenza virus subtype H5, the electrochemical label may become distant from or close to the electrode, or may be separated from the aptamer, thereby changing in electrochemical signal. In this way, based on changes in the signal, the presence or concentration of the avian influenza virus subtype H5 may be determined.

The detection method may further include separating the avian influenza virus subtype H5-aptamer complex from a reactant comprising the sample and the aptamer. The separation step may be performed after forming the avian influenza virus subtype H5-aptamer complex and before measuring the signal from the avian influenza virus subtype H5-aptamer complex. This separation step may be performed using membrane filtration, secondary fixed carrier adsorption, magnetic separation or centrifugation. Also, when the aptamer is immobilized on the substrate, it may be separated through a washing process. When the aptamer is immobilized on the secondary fixed carrier, it may be separated through a detachment or elution process. Here, the secondary fixed carrier of the aptamer may be, for example, silicon, polyethylene, or polypropylene, having a specific pore count and thickness. The optical label attached to the aptamer may be a fluorescent material. For example, the fluorescent material may be fluorescein, Cy3 or Cy5. The signal generated from the separated avian influenza virus subtype H5-aptamer complex may be measured using, for example, fluorometry or a radioisotope detection method. Specifically, a kit on which aptamer A1, aptamer A11, aptamer A12 and aptamer A13 are immobilized is provided, in which aptamer A1 is coupled with an optical label for emitting green fluorescence, aptamer A11 is coupled with an optical label for emitting red fluorescence, aptamer A12 is coupled with an optical label for emitting blue fluorescence, and aptamer A13 is coupled with an optical label for emitting yellow fluorescence. When a sample containing the H5N1 virus is reacted with the kit, the intensity of green fluorescence changes, whereby the presence of the H5N1 virus in the sample may be detected. When a sample containing the H5N2 virus is reacted with the kit, the intensity of red fluorescence changes, whereby the presence of the H5N2 virus in the sample may be detected. When a sample containing the H5N3 virus is reacted with the kit, the intensity of blue fluorescence changes, whereby the presence of the H5N3 virus in the sample may be detected. When a sample containing the H5N8 virus is reacted with the kit, the intensity of yellow fluorescence changes, whereby the presence of the H5N8 virus in the sample may be detected.

Figure 2:
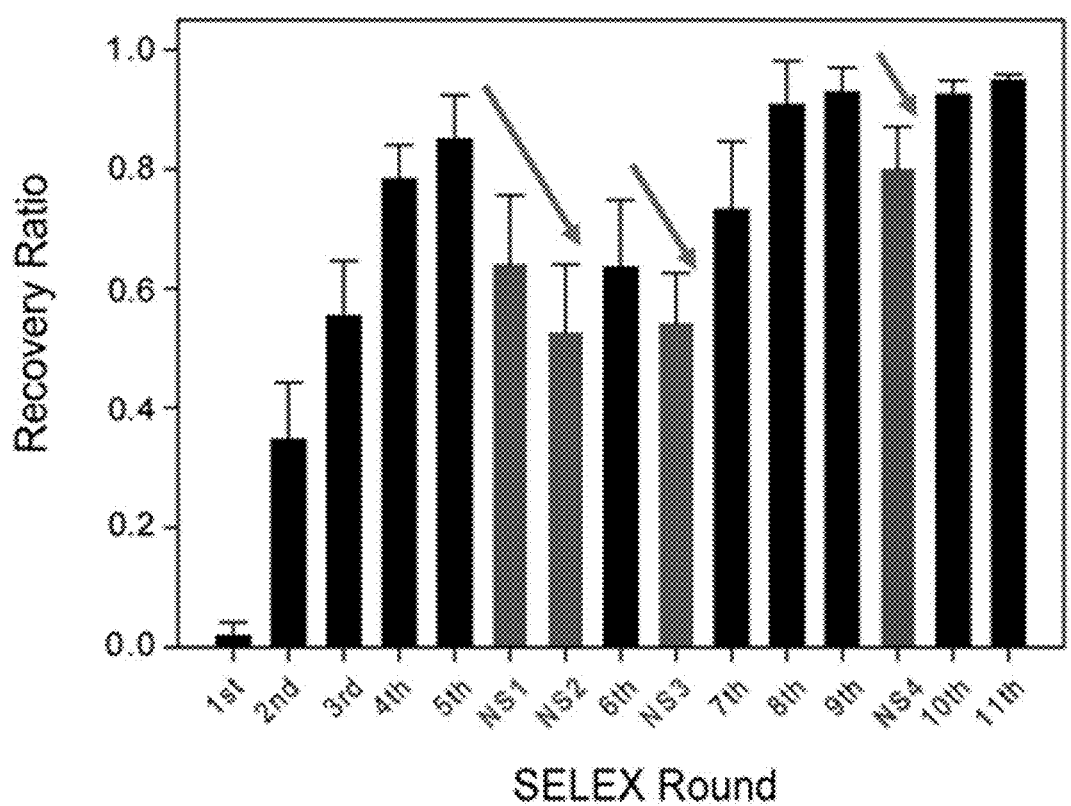
FIG. 2 is a graph showing the recovery ratio of ssDNA binding to hemagglutinin, which is a surface protein of avian influenza virus subtype H5 in the ssDNA library used in each selection round.

A better understanding of the present invention is given through the following examples, which are merely set forth to illustrate, but are not construed to limit the scope of the present invention. In the following examples, selected was ssDNA specifically binding to each of influenza A H5N1 (A/Hong Kong/483/97) strain HA (hereinafter, referred to as "H-12"), influenza A H5N1 (A/bar-headed goose/Qinghai/14/2008) strain HA (hereinafter, referred to as "Hg-2"), influenza A H5N1 (A/Vietnam/1994/2004) strain HA (hereinafter, referred to as "V-16"), influenza A H5N1 (A/Cambodia/R0405050/2007) strain HA (hereinafter, referred to as "C-8"), influenza A H5N1 (A/duck/Hunan/795/2002) strain HA (hereinafter, referred to as "HN-8"), influenza A H5N1 (A/Indonesia/5/2005) strain HA (hereinafter, referred to as "IN-3"), influenza A H5N1 (A/Egypt/2321-NAMRU3/2007) strain HA (hereinafter, referred to as "EG-2"), influenza A H5N1 (A/Hubei/2010) strain HA (hereinafter, referred to as "HB-16"), influenza A H5N1 (A/Japanese white-eye/Hong Kong/1038/2006) strain HA (hereinafter, referred to as "JW-1"), influenza A H5N1 (A/goose/Guiyang/337/2006) strain HA (hereinafter, referred to as "G-8"), influenza A H5N2 (A/American green-winged teal/California/HKWF609/2007) strain HA (hereinafter, referred to as "A-17"), influenza A H5N3 (A/duck/Hokkaido/167/2007) strain HA (hereinafter, referred to as "HK-12"), and influenza A H5N8 (A/duck/NY191255-59/2002) strain HA (hereinafter, referred to as "D-14"). Particularly, for H-12, ssDNA was selected through Examples 1 to 5, after which, for Hg-2, ssDNA was selected through Examples 1 to 5, after which, for another HA, ssDNA was selected through Examples 1 to 5. In FIG. 2, the value of the recovery ratio in each SELEX round indicates the average of the measured values during the procedure of selecting 13 HA species. The 13 HA species were purchased from Sino Biological Inc. (Beijing, China).

<Example 1> Preparation of ssDNA (Single-Stranded DNA) Library

An ssDNA library comprising a single-stranded DNA oligonucleotide was synthesized. The ssDNA library is represented by 5'-GCAATGGTACGGTACTTCC (SEQ ID NO:14)-N30-CAAAAGTGCACGCTACTTTGCTAA (SEQ ID NO:15)-3', both termini of which are composed of fixed base sequence regions in which the primer pair is annealed, and the center of which has a randomly arranged base sequence region (N30). Here, N30 is composed of 30 random A, G, T, and C bases, and the number of bases is not necessarily limited to 30. Through repeated PCR and cloning of SELEX, any number of bases may be added to or removed from the 30 bases.

<Example 2> Binding of Magnetic Bead and Surface Protein Hemagglutinin (HA) of Avian Influenza Virus Subtype H5

0.5 mg of magnetic beads having nickel and nitrilotriacetic acid covalently fixed to the surface thereof (HisPur™ Ni-NTAThermo) was washed three times with an equilibrium buffer (PBS, 0.05% Tween-20 Detergent, 10 mM imidazole, pH 8.0) and suspended in 100 μL of the equilibrium buffer. The surface protein hemagglutinin (HA) of avian influenza virus subtype H5 in powder form, having a polyhistidine-tag attached to the end (C-terminus) of the carboxyl group side thereof, was dissolved at a concentration of 0.1 mg/mL in purified water, and 50 μg of the dissolved polyhistidine-tag (His-tag)-attached avian influenza virus HA was dissolved in an equilibrium buffer, mixed with a magnetic bead solution, and allowed to react at 24° C. for 1 hr, thereby immobilizing HA on the magnetic beads.

<Example 3> Magnetic Bead-SELEX (1) Selection of ssDNA

The ssDNA library prepared in Example 1 was dissolved in purified water, heated at 95° C. for 10 min, treated at 4° C. for 15 min, and incubated at room temperature for 5 min, after which the resulting solution was suspended in a PBS buffer containing the HA-bound magnetic beads prepared in Example 2 and then reacted at 25° C. for 1 hr. The separation of unreacted ssDNA using a magnetic stand and three procedures of rinsing with a PBS buffer were performed, after which the resulting mixture, comprising avian influenza virus subtype H5 HA-bound magnetic beads and ssDNA, was heated at 95° C. for 10 min, thus eluting ssDNA from the magnetic beads. The eluted ssDNA was separated from the magnetic beads using a magnetic stand.

The amount of ssDNA thus selected was amplified through PCR. Before amplification, purification was carried out using a purification kit (MinElute PCR Purification kit, QIAGEN). Here, two primers for PCR were used, and particularly, the forward primer was used without terminal modification and the reverse primer was used in a manner in which the 5'-terminus was labeled with biotin so that a PCR product (dsDNA) having a double-helix structure was separated into ssDNA. Forward primer: 5'-GCAATGGTACGG-TACTTCC-3' (SEQ ID NO:16), and Reverse primer: 5'-bio-tin-TTAGCAAAGTAGCGTGCACTTTTG-3' (SEQ ID NO:17).

PCR was performed with a total of 50 μL volume, obtained by mixing 20 μL of 100 ng ssDNA, 2.5 μL of each of 10 μM two primers, and 25 μL of a PCR master mix under conditions of 95° C. (30 sec), 56.3° C. (30 sec), and 72° C. (10 sec), and was repeated ten times. The resulting PCR product was analyzed through electrophoresis using 2% agarose gel. Finally, the PCR product was purified using a MinElute PCR Purification kit (QIAGEN). Thereafter, only a desired single-stranded portion was separated from dsDNA, having a double-helix structure of the PCR product using magnetic beads (Dynabeads MyOne™ Streptavidin, Invitrogen) having streptavidin immobilized on the surface thereof. 50 μL of the PCR product was mixed with 950 μL of streptavidin-coated magnetic beads, reacted at room temperature for 10 min, and washed with 0.5 mL of a PBS buffer using a magnetic stand. Also, 500 μL of 200 mM sodium hydroxide (NaOH) was added thereto and reacted at room temperature for 10 min, and the separated ssDNA was recovered using a magnetic stand. The recovered ssDNA was purified and concentrated using an Amicon filter (Ultra-0.5, Millipore) kit, and the concentration thereof was analyzed. The purified and concentrated ssDNA was used for the next selection round. A total of 11 selection procedures resulted in 90% or more of the ssDNA mixed with the avian influenza virus subtype H5 HA binding to the avian influenza virus subtype H5 HA (FIG. 2).

(2) Negative Selection of ssDNA

In order to increase the selectivity of the selected ssDNAs for the surface protein of avian influenza virus, a total of four negative selection procedures was performed during the SELEX using magnetic beads to which all of 14 avian influenza HA species (H1 to H4, H6 to H13, H15 and H16 serum subtypes), having serum subtypes other than avian influenza virus subtype H5 and serving as the subject of negative selection, were bound. During the SELEX, the negative selection (NS) procedure was carried out a total of four times, including twice in succession after the fifth selection round, once after the sixth selection round, and once after the ninth selection round. The test method and conditions therefor were the same as in the selection procedure, but in the negative selection procedure, ssDNA bound to the subject of negative selection during the selection was discarded and ssDNA unbound thereto was recovered, amplified and then used for the subsequent selection round. The information about the avian influenza HA used for the negative selection is shown in Table 1 below.

TABLE 1

| Avian influenza virus species | HA type |
|---|---|
| A/California/07/2009 | H1 |
| A/Canada/720/2005 | H2 |
| A/Perth/16/2009 | H3 |
| A/mallard duck/Alberta/299/1977 | H4 |
| A/northern shoveler/California/HKWF115/07 | H6 |
| A/chicken/Netherlands/1/03 | H7 |
| A/pintail duck/Alberta/114/1979 | H8 |
| A/Chicken/Hong Kong/G9/97 | H9 |
| A/duck/Hong Kong/786/1979 | H10 |
| A/duck/Yangzhou/906/2002 | H11 |
| A/green-winged teal/ALB/199/1991 | H12 |
| A/black-headed gull/Netherlands/1/00 | H13 |
| A/duck/AUS/341/1983 | H15 |
| A/black-headed gull/Sweden/5/99 | H16 |

<Example 4> Cloning and Base Sequence Analysis

The ssDNAs finally obtained in Example 3 were subjected to PCR using primer pairs and then cloned using a cloning kit (TOPO TA cloning kit). In virus subtype H5 HA, approximately 20 colonies were obtained, and a plasmid was extracted from each colony to perform base sequence analysis.

<Example 5> Selection of Aptamer Through Analysis of Binding Affinity and Selectivity for Avian Influenza Virus Subtype H5 HA (1) The secondary structures of ssDNAs, the base sequences of which were analyzed in Example 4, were analyzed using an Mfold program (mfold.rna.albany.edu/?q=mfold; Zuker, M. Nucleic Acids Res. 2003, 31, 3406), and binding affinity and selectivity for avian influenza virus subtype H5 HA were measured, thus finally selecting an aptamer specifically binding to avian influenza virus subtype H5 HA.

(2) Based on the results of analysis of the secondary structures, approximately 10 ssDNAs estimated to have high binding affinity for avian influenza virus subtype H5 HA were chosen and then analyzed for selectivity. Compared to HA binding, ssDNAs in which the fluorescence intensity was reduced to less than 20% when reacting with 14 HA species having a serum subtype other than H5, as the subject of negative selection, were selected and then analyzed for binding affinity, from which the ssDNA having the greatest binding affinity was then selected. For binding affinity analysis, the avian influenza virus subtype H5 HA was suspended in a PBS buffer, mixed with fluorescence-labeled ssDNA at different concentrations (0, 5, 10, 50, 200, and 500 nM), and then reacted under the same binding conditions (25° C. for 1 hr), as in SELEX. After the reaction, ssDNAs that were not bound to the target were removed through five processes of washing with a PBS buffer, and the fluorescence intensity of the avian influenza virus subtype H5 HA-ssDNA complex was measured using a fluorometer. The fluorescence intensity at each ssDNA concentration was plotted using a nonlinear regression method and a single-region saturation ligand binding method via a SigmaPlot program based on the equation of $F=B_{max}*C/(K_d+C)$ (wherein F is the fluorescence intensity, $B_{max}$ is the maximum binding position, $K_d$ is the dissociation constant, and C is the ssDNA concentration). The selectivity was analyzed by measuring binding affinity for magnetic beads to which all of 14 avian influenza virus HA species, used as the subject of negative selection, were bound. The test method and conditions therefor were the same as in the binding affinity analysis of fluorescence-labeled ssDNA aptamer (200 nM) for the avian influenza virus subtype H5 HA and the avian influenza virus HA used as the subject of negative selection. The fluorescence intensity thereof was measured, thereby selecting ssDNA having high fluorescence intensity in avian influenza virus subtype H5 HA-bound magnetic beads and relatively low fluorescence intensity in magnetic beads to which the HA serving as the subject of negative selection was bound. Compared to HA binding, ssDNA having relative fluorescence intensity reduced to less than 20% when reacting with 14 HA species having a serum subtype other than H5, as the subject of negative selection, was selected.

Final Selection Result

Figure 3A:
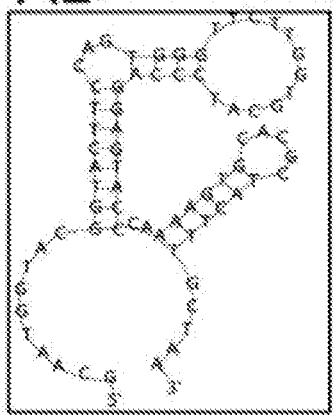
FIG. 3A to 3C shows the secondary structures of nucleic acid aptamers specifically binding to hemagglutinin, which is a surface protein of avian influenza virus subtype H5.
Figure 3A:
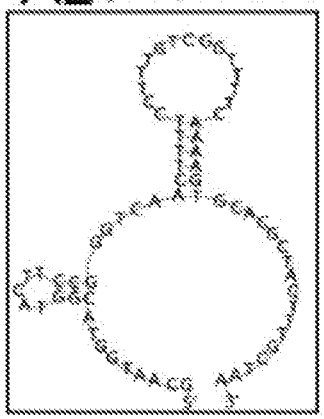
Figure 3A:
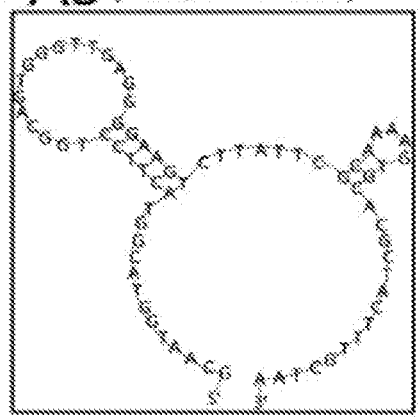
Figure 3A:
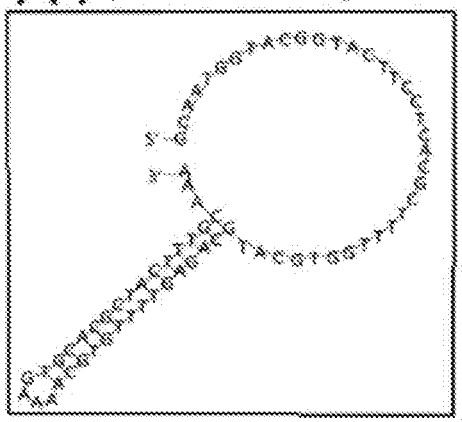
Figure 3A:
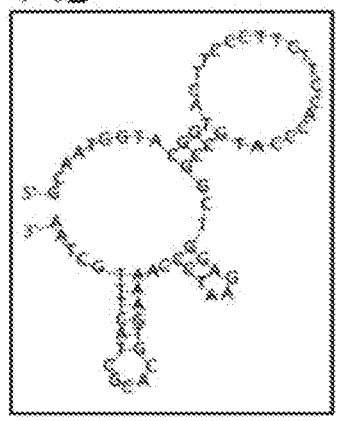
Figure 3B:
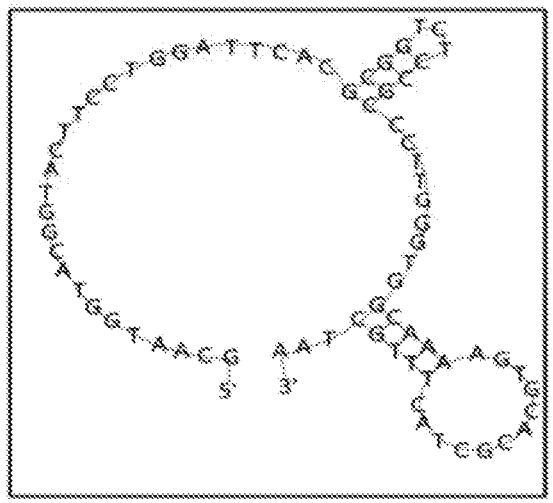
Figure 3B:
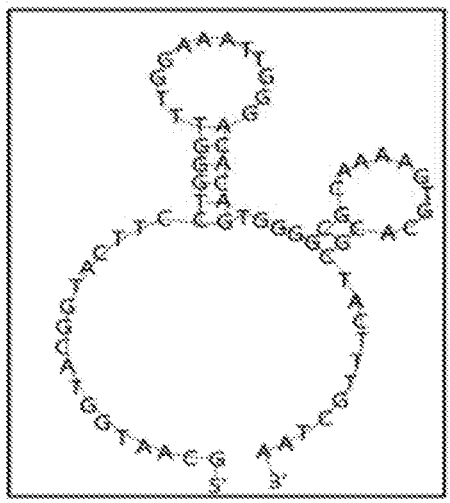
Figure 3B:
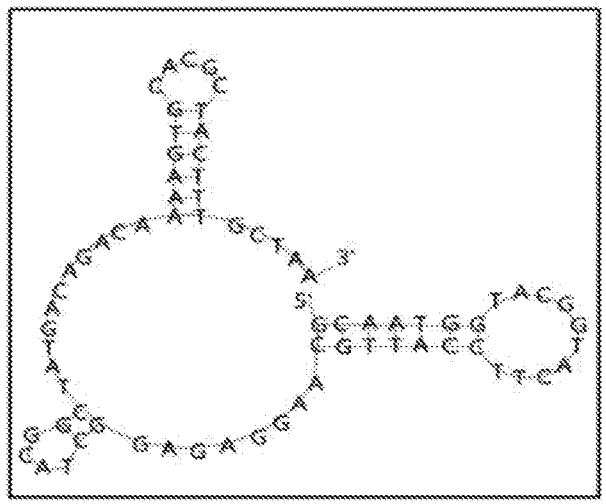
Figure 3B:
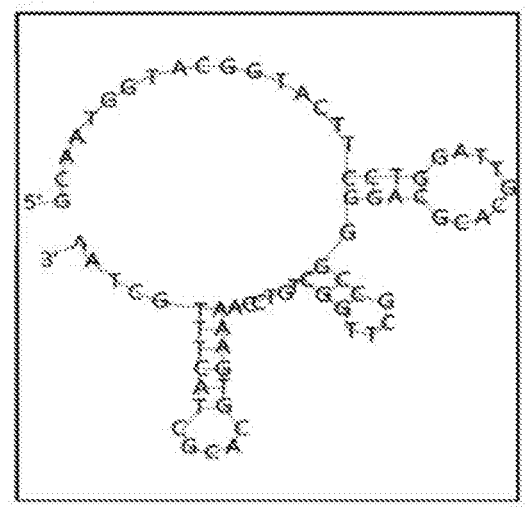
Figure 3C:
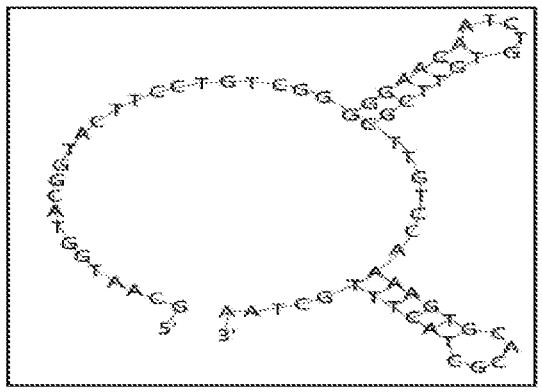
Figure 3C:
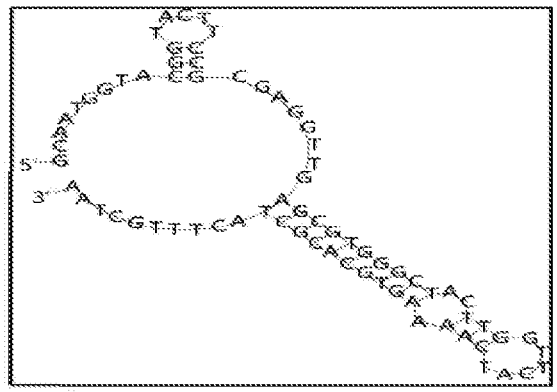
Figure 3C:
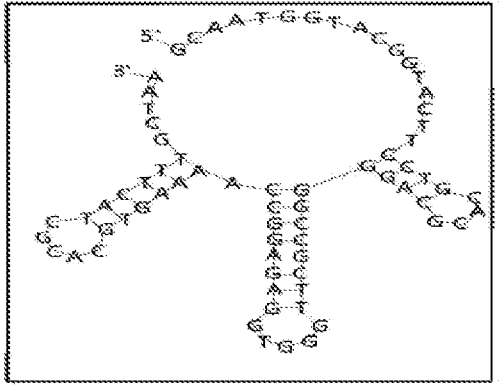
Figure 3C:
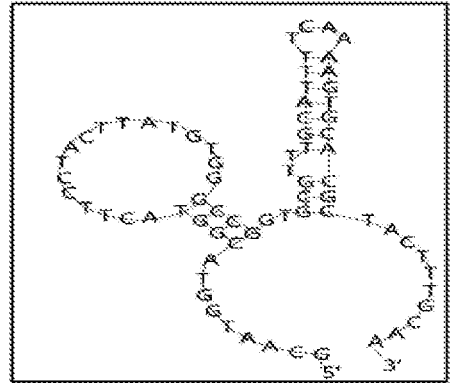
Figure 4:
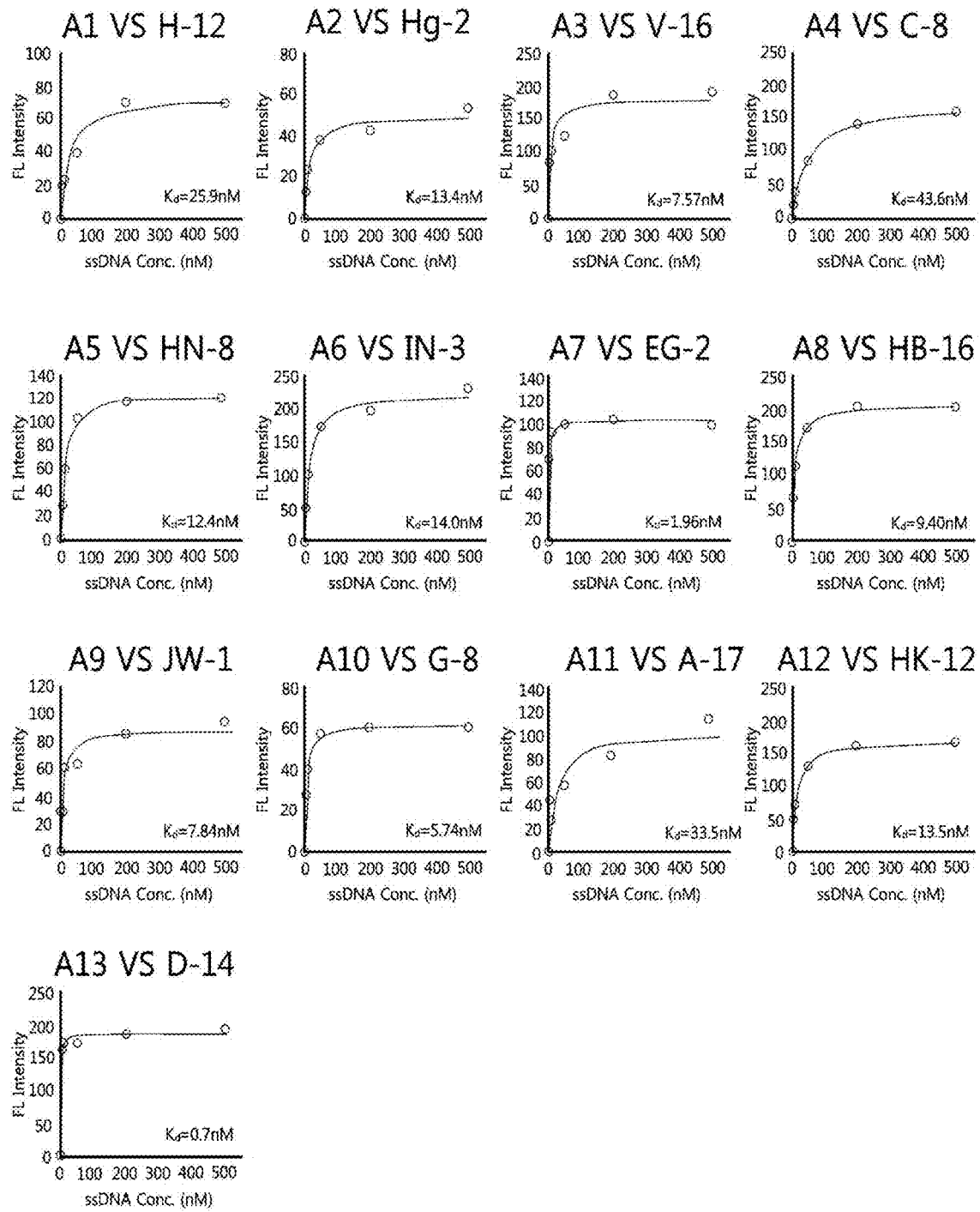
FIG. 4 shows the results of analysis of binding affinity of the nucleic acid aptamers specifically binding to hemagglutinin, which is a surface protein of avian influenza virus subtype H5.

Through the above procedures, ssDNA specifically binding to each avian influenza virus subtype H5 HA was selected. The results are shown in Table 2 below and the secondary structure of each ssDNA is illustrated in FIG. 3A to 3C. The results of analysis of the binding affinity of ssDNA are shown in Table 2 and FIG. 4. As is apparent from Table 2, ssDNA (A1) having a base sequence of SEQ ID NO:1 exhibited very high affinity (dissolution constant: 25.9 nM) for influenza A H5N1 (A/Hong Kong/483/97) strain HA (H-12).

TABLE 2

| Name of ssDNA | Target virus subtype H5 HA | Base sequence of ssDNA specifically binding to target virus subtype H5 HA | Dissociation constant (nM) |
|---|---|---|---|
| A1 | H-12 | AGTGGGTTCTTGGTGCATCCCAGGAGTACC (SEQ ID NO: 1) | 25.9 |
| A2 | Hg-2 | GGGGTCAACTTTTCCTTTGTCGGTTTT (SEQ ID NO: 2) | 13.4 |
| A3 | V-16 | TGGCAGTGGGTTGAGGGGAAGTCTTATTCG (SEQ ID NO: 3) | 7.57 |
| A4 | C-8 | TCACGCTTTTGGTGCATGCAGAGTTTTGTG (SEQ ID NO: 4) | 43.6 |
| A5 | HN-8 | CTTCTTCCACCCATGCCGGCTGGAGAATCC (SEQ ID NO: 5) | 12.4 |
| A6 | IN-3 | TGGATTCACGCGGTCTCCGCCCTTGGGTGG (SEQ ID NO: 6) | 14.0 |
| A7 | EG-2 | TGGGTTTGGAAATTGGGACACAGTGGGGCG (SEQ ID NO: 7) | 1.96 |
| A8 | HB-16 | ATTGCAAGGAGAGGCTACGGCTATGACAGA (SEQ ID NO: 8) | 9.40 |
| A9 | JW-1 | TGGATTGCACGCAGGGGCCGCTTGGCTGTC (SEQ ID NO: 9) | 7.84 |
| A10 | G-8 | TGTCGGGGGAACAATCTGTGTTCGCTTGTC (SEQ ID NO: 10) | 5.74 |
| A11 | A-17 | GCGAGGTTGAGCGTGGGCTACTTGGTTCAT (SEQ ID NO: 11) | 3.5 |
| A12 | HK-12 | TGCACGCAGGGGCCGCTTGGGTGGAGAGGC (SEQ ID NO: 12) | 3.5 |
| A13 | D-14 | TACTTATGTGGGCCGGTGCGTTTGCATTTT (SEQ ID NO: 13) | 0.70 |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A nucleic acid aptamer specifically binding to hemagglutinin, which is a surface protein of an avian influenza virus subtype H5N8, the nucleic acid aptamer having the base sequence of SEQ ID NO: 13.

2. The nucleic acid aptamer of claim 1, wherein the nucleic acid aptamer includes a detectable label attached thereto.

3. The nucleic acid aptamer of claim 2, wherein the detectable label is an optical label, an electrochemical label, a radioisotope or a combination thereof.

4. A composition for detecting an avian influenza virus subtype H5N8, comprising the nucleic acid aptamer of claim 1.

5. A sensor for detecting an avian influenza virus subtype H5N8, comprising the nucleic acid aptamer of claim 1.

6. A kit for detecting an avian influenza virus subtype H5N8, comprising the nucleic acid aptamer of claim 1.

7. The kit of claim 6, wherein the kit is provided in a form of a chip configured such that the nucleic acid aptamer is immobilized on the chip, or in a form of a microarray configured such that the nucleic acid aptamer is immobilized on a substrate.

8. A method of detecting an avian influenza virus subtype H5N8, comprising:
   contacting a sample with the nucleic acid aptamer of claim 1, thus forming an avian influenza virus subtype H5N8-nucleic acid aptamer complex;
   measuring a signal from the avian influenza virus subtype H5N8-nucleic acid aptamer complex;
   analyzing the measured signal; and
   detecting a presence or concentration of the avian influenza virus subtype H5N8 in the sample based upon the analyzed measured signal.

9. The method of claim 8, further comprising separating the avian influenza virus subtype H5N8-nucleic acid aptamer complex from a reactant comprising the sample and the nucleic acid aptamer.

* * * * *